United States Patent [19]

Paluch

[11] Patent Number: 4,714,078
[45] Date of Patent: Dec. 22, 1987

[54] INSERT FOR HEATED HUMIDIFIER USED IN RESPIRATORY THERAPY

[76] Inventor: Bernard R. Paluch, 500 Glenn Ave., Wheeling, Ill. 60090-6016

[21] Appl. No.: 884,775

[22] Filed: Jul. 9, 1986

Related U.S. Application Data

[63] Continuation-in-part of Ser. No. 677,394, Dec. 3, 1984, abandoned.

[51] Int. Cl.⁴ .............................................. A61M 16/00
[52] U.S. Cl. ................................................ 128/203.17
[58] Field of Search ...................... 128/203.17, 203.27, 128/204.17

[56] References Cited

U.S. PATENT DOCUMENTS

| | | | |
|---|---|---|---|
| 1,648,547 | 11/1927 | Goodfellow | 128/203.17 X |
| 3,873,806 | 3/1955 | Schossow | 128/203.27 X |
| 4,201,204 | 5/1980 | Rinne et al. | 128/203.27 |
| 4,303,601 | 12/1981 | Grimm et al. | 128/203.27 X |
| 4,369,776 | 1/1983 | Roberts | 128/203.17 X |

FOREIGN PATENT DOCUMENTS

| | | | |
|---|---|---|---|
| 116386 | 1/1970 | Denmark | 128/203.27 |
| 240537 | 10/1925 | United Kingdom | 128/203.27 |

Primary Examiner—Edward M. Coven
Attorney, Agent, or Firm—Eugene I. Snyder

[57] ABSTRACT

There is provided for a heated humidifier used in respiratory therapy a method of lowering the heating cost, reducing the waste of humidifier fluid, lowering the compliance volume and reducing the labor costs attending water level maintenance by placing a removable, space filling, volume reducing insert into the reservoir of existing heated humidifiers. The resulting modified humidifier may be used both for adult patients as well as pediatric and neonatal patients.

3 Claims, 9 Drawing Figures

INSERT FOR HEATED HUMIDIFIER USED IN RESPIRATORY THERAPY

CROSS REFERENCE TO RELATED APPLICATION

This application is a continuation-in-part of my copending application, Ser. No. 677,394, filed Dec. 3, 1984, now abandoned, all of which is hereby incorporated by reference.

BACKGROUND OF THE INVENTION

This invention relates to heated humidifiers used in respiratory therapy. More particularly, it relates to a method of reducing the volume in the reservoirs of existing humidifiers and an apparatus for achieving such volume reduction cheaply and efficiently and for expanding the use of the humidifier to a larger universe of patients.

The use of heated humidifiers in respiratory therapy is a widespread and commonly employed practice in hospitals. Given the necessity for imposing stringent cost controls on spiraling hospital expenses, cost-cutting improvements attending the use of such humidifiers is quite desirable. The problems exhibited by prior art humidifiers, and the present needs to be addressed, are diverse. At the outset it is essential to recognize that any improvement should be compatible with existing equipment. Since the impetus for improvement is lower cost in patient care, any improvement requiring the replacement of old equipment, or expensive modification of existing apparatus, is an illusory benefit at best, and is self-defeating at worst. The method herein provides a simultaneous solution to the variety of problems associated with several designs of heated humidifiers used in respiratory therapy and to the needs of hospitals in achieving a significant cost reduction attending their use.

Heated humidifiers are used to add sterile water vapor to gas being inhaled by patients whose upper airway has been bypassed or rendered ineffective in preventing desiccation of the respiratory mucosa. Such patients typically have an endotracheal or tracheotomy tube in their trachea so that the normal physiological means (the nose, mouth, trachea, etc.) of heating and humidifying inhaled gas has been bypassed. The heated humidifier warms and humidifies the gas by causing it to bubble through a volume of heated sterile water. The function of the heated humidifier is to heat and humidify the gas to an appropriate, constant temperature and saturation level so that upon entry into the tracheal tube its temperature is between 85° and 98.6° F. and it is saturated with sterile water vapor. To date, this has been done by using humidifiers with a relatively large water reservoir, since a large volume aids in minimizing temperature fluctuation once the operational temperature has been achieved and extends the time between refills. However, since the reservoir of the heated humidifiers and the sterile water contained therein requires change at least every 24 hours to insure maintenance of sterile conditions, a large volume reservoir leads to appreciable waste by incomplete utilization of the sterile water. Such waste is an additional cost factor of patient care. For example, one heated humidifier commonly used has a reservoir whose volume from "empty" to "refill" is 475 ml, with a volume from "refill" to "full" of 300 ml. Therefore the amount of sterile water discarded per day may vary between 475 and 775 ml, which equates to a daily waste between $1.50–2.50 per humidifier.

Another undesirable characteristic of heated humidifiers with a large reservoir is the relatively high compressible volume, or compliance volume, attending their size. By compliance volume is meant that volume of gas used for development of pressure in the humidifier; it is an amount which plays no role in the ventilation of the patient, but is an amount of gas needed to be supplied by the ventilator. The total gas supplied by the ventilator is the sum of the volume supplied to the patient plus the compliance volume of the system (ventilator, humidifier, and breathing circuit). The compliance volume itself varies with the water level in the reservoir, and unless the reservoir is supplied with a constant level control the compliance volume varies during use. This leads to a varying gas volume delivered to the patient since the total gas output from the ventilator typically is constant at a given setting. Using the heated humidifier previously exemplified, the compliance factor with the water level at "full" is 1.0 ml per cm of water pressure. At a peak inspiratory pressure of 40 cm of water 40 ml must be added to the ventilator output merely because of humidifier compliance. When the water level is at "refill" the compliance factor is 1.3 ml per cm of water pressure, leading to an additional 52 ml ventilator gas output needed to deliver proper gas volume to the patient.

Since the compliance volume represents an amount of gas not utilized by the patient, it also represents wasted gas, an additional cost for which no benefit is received. Because wasted gas nevertheless is heated and humidified, which requires the expenditure of energy, the compliance volume also represents an energy cost for which no benefit is received.

The compliance volume increases with an increase in peak inspiratory pressure. As the pressure necessary to ventilate the patient increases, the significance attached to the compliance volume increases because the latter robs a proportionately larger share of gas of the ventilator output. This becomes especially significant in pediatric and neonatal patients, whose inelastic lungs require a peak inspiratory pressure about twice that for adult patients, but whose gas volume need is perhaps only 5% to 25% that of the adult. In such cases, a relatively large fraction—perhaps from about ¼ to about ½—of the ventilator output is not utilized, thereby leading to gross waste. The compressible volume is directly related to the internal volumes of the system components; a higher compressible volume means that the internal volume is higher. In turn, that means that a larger volume must be inhaled by the patient to create the negative pressure needed to trigger the inspiratory cycle of the ventilator. Neonatal patients, as a rule, cannot inhale sufficient volume to trigger the ventilator when an "adult-size" humidifier is used. As a result manufacturers have developed pediatric-size humidifiers, which means that hospitals with both pediatric and adult patients need to acquire and maintain two sizes of humidifiers, further adding to patient cost.

The large reservoir also requires a relatively high wattage heater, both to bring the larger volume of water to temperature in a reasonable time and to maintain it once there. The result is a relatively high degree of energy waste. A desirable improvement would be to supply only enough heat as is necessary to vaporize that amount of water required to achieve the temperature and humidity desired.

The marketplace needs a heated humidifier with less waste and greater utility. It needs a unit with less energy loss, less waste of humidifying water, lower compliance volume, and reduced labor costs attending the maintenance of reservoir water level; it needs a unit usable with both neonatal and adult patients and it needs to achieve all these ends without requiring replacement of existing units by expensive new equipment.

The invention herein is remarkable not only in its simplicity but also in its achieving the varied needs of the user efficiently and at low cost. The invention herein is a method of maintaining in the reservoir of large volume humidifiers a relatively small, and in one embodiment a constant, volume of water so as to use little energy above that necessary to vaporize the required amount. Because the water volume is small there is little waste when the reservoir is changed. Because the resulting compressible volume of the reservoir is small the compliance volume is reduced substantially, so that the same humidifier is usable both for pediatric and neonatal patients as well as adults. Finally, the embodiment incorporating constant water level control eliminates the labor costs and ventilation interruptions caused by periodic refilling.

SUMMARY OF THE INVENTION

The purpose of the invention herein is to adapt existing heated humidifiers used in respiratory therapy so as to provide a water reservoir with substantially reduced volume. In a specific embodiment the invention is a removable insert occupying at least 35% of the volume of the reservoir of a humidifier and which receivably accommodates in close cooperation a tower with gas dispersing means, a heater well and a well for a temperature sensor, all of which descend from the top or cover of said humidifier with the cover being removably attached to the reservoir containing said insert.

DESCRIPTION OF THE INVENTION

Figure 1:
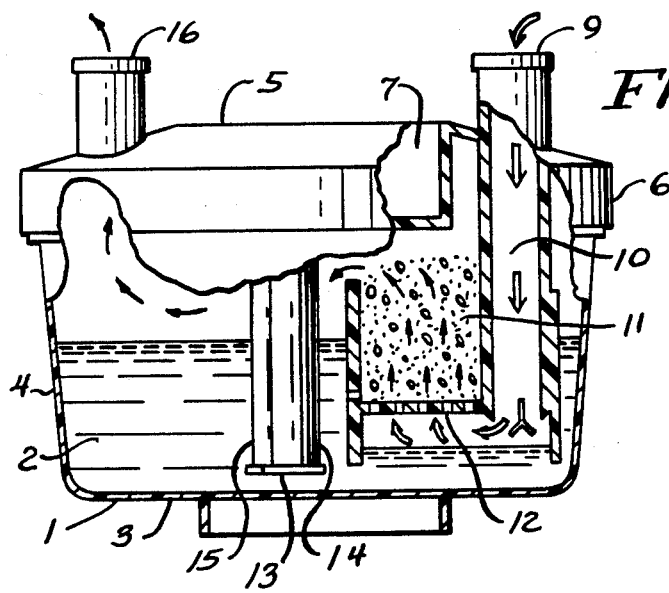
FIG. 1 is a cutaway view of an assembled heated humidifier.
Figure 2:
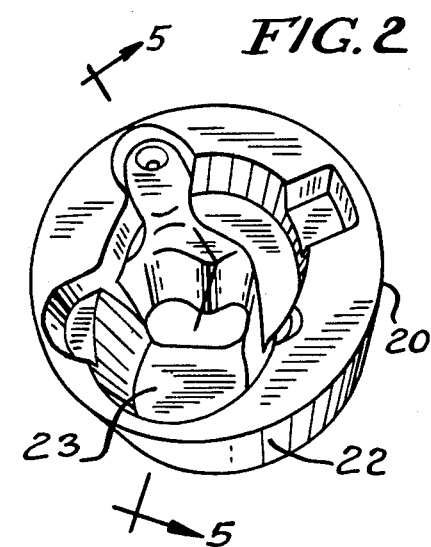
FIG. 2 is a top perspective view of the insert of this invention.
Figure 3:
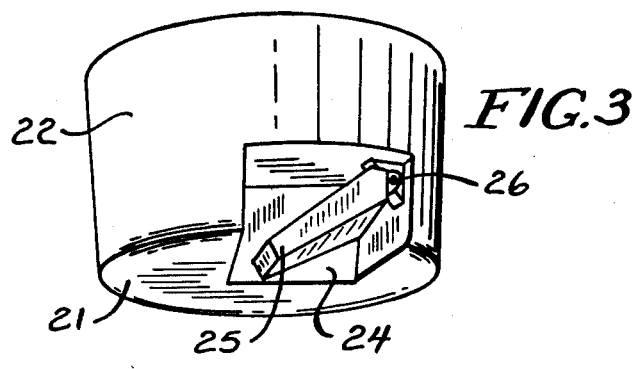
FIG. 3 is a side perspective view of said insert.
Figure 4:
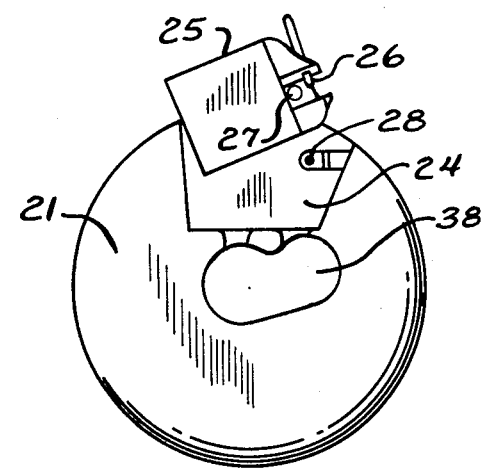
FIG. 4 is a bottom view of said insert with the float removed and inverted.
Figure 5:
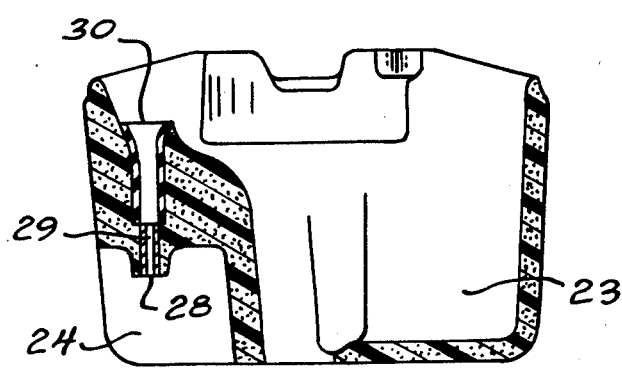
FIG. 5 is a cutaway view through 5—5 of FIG. 2.

This invention is directed toward heated humidifiers used in respiratory therapy. Such humdifiers have varied designs, with the description below being merely illustrative and exemplary of a commonly employed design. Although my invention is adaptable to many designs, it is especially directed toward humidifiers of the described design. Such an apparatus as assembled is depicted in FIG. 1 and is characterized by a lower portion, 1, formed as a reservoir, 2, for sterile water. The lower portion is generally tub shaped with a bottom wall, 3, and a circular side wall, 4. The lower portion is adapted, generally by a screw thread at the outer surface of the uppermost part of the lower portion, to be removably attached to a top portion, 5, or cover, usually having two ports and a double well. The cover is generally circular with a side wall, 6, whose inner diameter receives the uppermost part of the lower portion and which is threaded so as to receive the aforementioned screw threads on said lower portion. The top is generally planar to slight convex with a cylindrical depression, 7, at its center containing two openings, 8. The gas entry port, 9, is the upper terminus of a conduit, 10, whose lower terminus is open and which leads into a tower, 11. The tower is a tubular member open at both its top and bottom. Near the bottom of the tower is a perforated disc, 12, to which is attached the lower terminus of conduit 10 so that the conduit is in open communication with the underside of the disc. Near the center of the underside of the cylindrical depression in the cover, but slightly off center, secured thereto and depending therefrom is a double well, 13, descending into the reservoir, and terminating at a point slightly above the bottom of the reservoir when the latter is releasably attached to the cover. Each of the wells is a tubular member with a closed lower terminus and an open upper terminus, and each member is attached to the underside of the cylindrical depression in the cover such that its open upper terminus mates with one of the openings 8. Thus the interior of each well is in open communication with the top surface of the cover, but is sealed off from the contents of the reservoir.

One of the wells, 14, receivably accommodates a heating element and the other of the wells, 15, receivably accommodates a temperature sensor. The sensor may be a simple thermometer or a more sophisticated sensor, such as a thermocouple or thermistor which is part of a temperature regulating circuit. The wells extend into the water contained in the reservoir when the latter is filled to its operating level and is firmly attached to the cover. The heating element maintains the water in the reservoir at a more-or-less constant temperature which saturates the gas with moisture at the desired temperature upon delivery to the patient. The amount of heat needed is a function, *inter alia,* of gas flow, water volume, and desired relative humidity. The second port, 16, is the gas exit port leading to the patient. The gas exit port, or optionally a third port, may be equipped with means of replacing the water used in the reservoir. Maintenance of a constant liquid level is not a universal design characteristic of existing heated humidifiers toward which my invention is directed, but it is to be clearly understood that my invention encompasses such apparatus.

In operation, the reservoir 2 is releasably attached to the top by a screw thread. When the reservoir is firmly attached it is filled with water to a level at least sufficient to fully immerse the perforated disc. It is to be emphasized that this is the *minimum* amount of water required for proper operation, with the maximum water content corresponding to a level sufficient to immerse about two-thirds of the double well. The gas used in respiratory therapy, which may vary between air and virtually pure oxygen, but in any event is well known to those skilled in the art, is led into the gas entry port into the tower and emerges below the perforated disc, hence below the water line. As the gas is still contained within the tower it percolates through the perforated disc which disperses the gas into fine bubbles. As the small gas bubbles continue to rise through the water they become saturated with the heated water and exit through the gas exit port as a heated, moisture-laden gas stream. The gas flow is indicated by the arrows in FIG. 1.

The invention herein consists in reducing the volume of the original or first reservoir, and in providing a second reservoir containing a limited amount of water sufficient to perform the role of humidifying the gas by placing in the first reservoir a removable, noncompressible, nonabsorbent, and preferably a sterilizable and reusable volume-filling insert. It is desired that the insert be noncompressible so it is impermeable to the pressurized gas delivered by the ventilator. Such noncompressibility means that the insert will reduce the total compressible volume within the humidifier. It is desired that the insert be nonabsorbent so that it has no "memory" as to its prior environment, i.e., it does not retain water or a sterilizing agent. It is desired that it be sterilizable because of the need to provide a sterile system holding the sterile water used in humidifiers. It is desired that the insert be reusable to allow cost reductions from its repeated use. But if the cost of hospital sterilization becomes greater than the cost of a sterile disposable insert, a disposable insert may be used, in which case it need not be reusably sterilizable.

Any material which is noncompressible, nonabsorbent, and preferably sterilizable may be used in the practice of this invention. Perhaps the most preferred material of construction is closed-cell polyurethane. This is a lightweight, rigid foam characterized by numerous discrete, noncommunicating cells having a wall around each cell, with a smooth skin on the outer surface. A foam of different composition with substantially similar properties also is satisfactory. Fabrication of the insert using materials and techniques commonly employed in blow molding or injection molding in principle is quite acceptable, although the aforementioned techniques are used only with difficulty in products not having axial symmetry.

The insert of this invention effects a substantial reduction in humidifier volume. Volume reduction is of two kinds. On the one hand there is a reduction in the maximum volume of water which can reside in the humidifier at any time. On the other hand there is a reduction in gas volume in the humidifier. Both kinds of volume reduction depend upon the design of the humidifier and the insert, but there is a reduction in maximum water volume of at least 35%, and the reduction often is between about 50% and about 85%. That is, the insert displaces at least about 35% of the volume of the reservoir, and preferably displaces between about 50 and 85% of the maximum water volume. The insert contains a second reservoir which accommodates the heating element and gas dispersing means of the heated humidifier and which acts as a second reservoir for a very limited amount of water. The second reservoir is so constructed as to provide an adequate depth and volume of water for good gas-water contact and for heater-water contact.

Because the purposes of this invention are achieved by having a relatively small volume of water in the humidifer at all times, a disproportionately large expenditure of labor would be needed to maintain a working amount of water unless provision was made to automatically maintain the water at a constant or near constant level. Since labor-intensive activity is contrary to the very purpose of this invention, one embodiment employs a means of maintaining a constant water level. Such means are varied in design and method of operation. For example, such means may comprise an electronic sensor of water level operating a solenoid-actuated valve to a sterile water delivery system, thereby adding water whenever the water level drops below some predetermined point. A less sophisticated, more practical system comprises a float valve acting as a flow controller in a sterile water delivery system. An even more primitive control system may be envisaged as consisting of a large reservoir external to the heated humidifier connected to the reservoir of the insert by a siphon system, where the relatively large volume of the external reservoir serves to maintain a constant level of water in the reservoir of the insert. The particular means employed are not important in the context of the method which is the invention herein, although not all means are necessarily equivalent, and any means which perform the function of maintaining a constant water level in the insert reservoir is contemplated as being within the scope of this invention.

An insert which achieves all the goals stated herein is depicted in FIGS. 2-6. The insert 20 is a generally tub-shaped solid constructed of material which is nonadsorbent, noncompressible, and preferably sterilizable. It is contoured to fit the interior reservoir of the heated humidifier rather closely and is so dimensioned as to occupy a substantial fraction of the total available volume of the first reservoir, i.e., at least about 35%. The insert has the overall appearance of a conic section, with a planar bottom, 21, and a circular side, 22. The insert is formed with a depression, 23, which extends downward from the top of the insert and functions as a second reservoir. The depression is dimensioned and shaped to closely receivably accommodate the double well 13 and tower 11 extending into the lower portion 1 from the cover of the heated humidifier. The bottom of the depression or second reservoir is in open communication with the first reservoir via the opening, 38, so that water placed in the first reservoir flows freely into the second reservoir. Adjacent to the second reservoir is formed a chamber, 24, also in open communication with the first reservoir, said chamber containing a float valve, 25. The float valve is pivotally connected at one end to the top of the chamber by hinge means, 26, and the upper surface of the valve is fitted with conduit closing means, 27.

At the upper surface of the chamber positioned immediately above the conduit closing means is a port, 28, which is the lower terminus of a conduit, 29, extending from the top of the chamber through the body of the insert with its upper terminus being the port, 30, located at the top surface of the insert. Since the float valve is pivotally connected or hinged at one end, water entering through port 28 causes the water level in the chamber to rise, thereby raising the float. The conduit closing means, which may be merely a pad or circular disc of a flexible rubbery material in adhering contact with the float surface, then is forced up against the port 28, sealing off the conduit and preventing further water flow.

The figures depict an insert with a wall between the second reservoir and the chamber 24. Having a wall enhances the space-filling properties of the insert and also prevents the wave action in the second reservoir 23 which is caused by rapidly bubbling gas, from causing chatter of the float valve. Such chatter could lead to improper water level control, hence the presence of the wall is a desirable design feature. However, the prior comments should make it clear that the wall is not an indispensable feature of the invention.

In one embodiment the port 30 terminates in a tapered or conical bushing of an elastic material so as to provide for a blind entry or guide for a tube, 31, and also to provide for a tight seal around said tube. This tube delivers water to the humidifier from the sterile water source and is one terminus of a water transfer set. Such a set consists of said tube, a tubular elbow, 32, flexible tubing, 33, a drip chamber, 34, with a cap terminating in a pointed, tubular puncture spike.

The upper terminus of delivery tube 31 is sealed to the open top portion, 36, or port of the elbow. To the top portion of the elbow is also connected in a watertight manner the lower end of a segment of flexible tubing, 33, whose upper end is mated with the drip chamber, 34, with a watertight connection. The drip chamber is of conventional design and has a cap terminating in a pointed, tubular puncture spike. The lower end, 35, of the elbow 32 is dimensioned as to tightly fit over the gas exit port 16 on the top of the humidifier. Extending laterally from elbow 32 is another tubular portion, 38, terminating in a port, 37, which is connected to the breathing circuit.

As stated above, the lower end, 35, of the elbow fits tightly over the gas exit port of the top portion of the humidifier. The tube 31 is firmly attached to the top, 36, of the elbow, the said top also having an opening in its wall directly above the tube 31, which opening is the bottom terminus of a port which connects said tube to the flexible tubing. Such tubing terminates at its other end in a drip chamber, which permits an operator to readily see how rapidly water is flowing to the humidifier. The cap to the drip chamber contains a pointed tubular spike with a needle-like structure which serves to puncture and connect to the source of sterile water. Side port 37 is connected to the breathing circuit and is the passageway for the heated and humidified gas.

Figure 7:
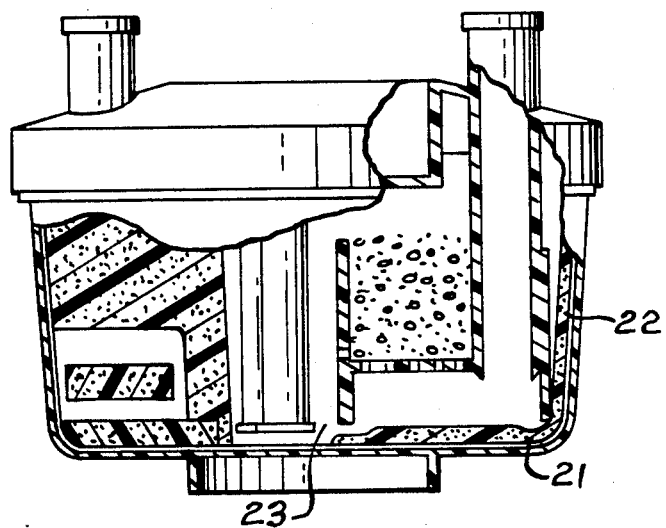
FIG. 7 is a cutaway view of an assembled heated humidifier with the insert in place.
Figure 6:
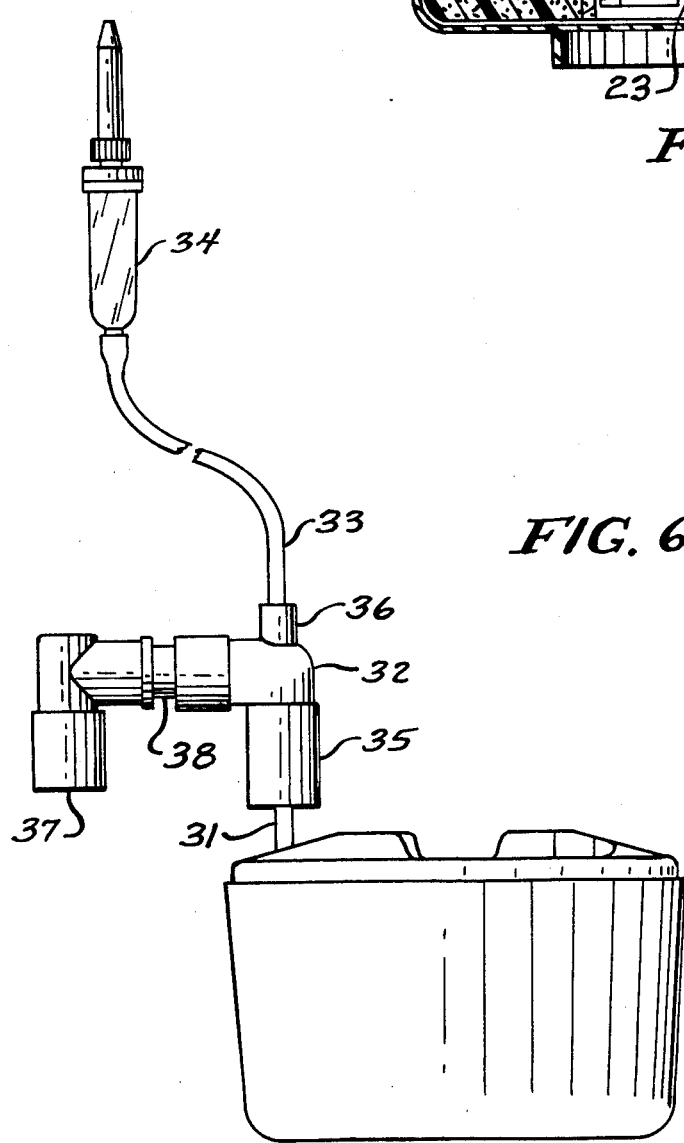
FIG. 6 depicts the water transfer set in place.

FIG. 7 shows the insert in place in the apparatus depicted in FIG. 1 and aids in visualizing its operation. Water enters from the water delivery system through the top of the conduit, 29, entering the chamber, 24, through the bottom terminus 28. The float valve, 25, controls whether water enters and tends to maintain a constant level of water in the reservoir. Water flows from the chamber into the first reservoir, thence into the second reservoir which is in open communication with the first reservoir. The water in the second reservoir is heated by the element in the cover and extending into 14, and air entering port 9 is dispersed as small bubbles by the disc 12 and passes through the heated water, thereby providing a constant level of water vapor in the gas delivered to the patient. As water from the second reservoir is evaporated, the float valve opens so as to admit additional water into the system, the float valve then closing when the predetermined level of water has been reached. In this way there is present in the heated humidifier at all times only a relatively small amount of water. The total available gas volume in the reservoirs of the heated humidifier is also relatively small, which lends to a low compliance volume. Since the water level in the reservoirs is automatically maintained little expenditure of labor is necessary to insure proper operation of this aspect of the humidifier.

Figure 8:
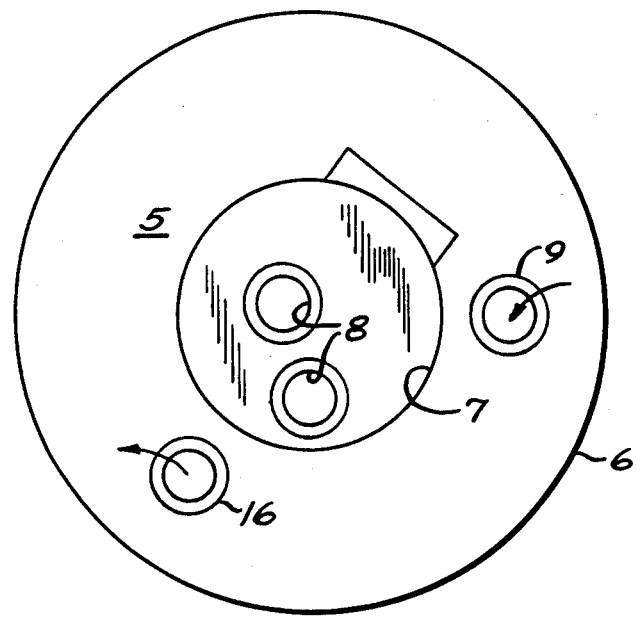
FIG. 8 is a top view of the cover in FIG. 1.
Figure 9:
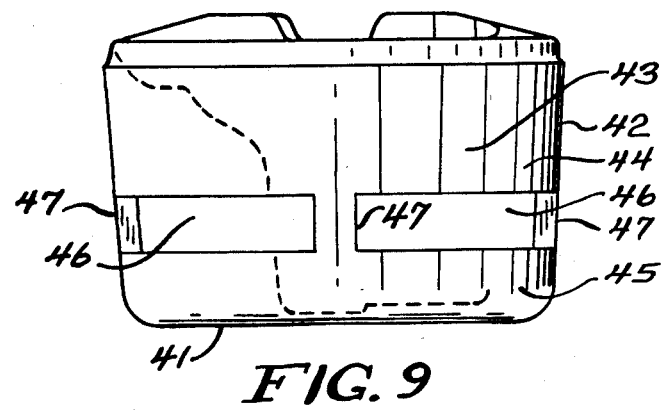
FIG. 9 is an alternate embodiment of the insert of this invention.

Although the description above has been largely directed to an insert which maintains a constant water level, an embodiment lacking this feature is feasible, even though it may be less desirable. One such device may be derived from that in FIG. 2-6 simply by omitting the conduit, 29, port 28, float valve 25, and chamber 24. Yet another such analogous device is shown in FIG. 8, where the generally tub-shaped solid insert is of a nonadsorbent, noncompressible, and preferably sterilizable material contoured to fit the first reservoir 2 of the heated humidifer rather closely and is so dimensioned as to occupy a substantial fraction of the total available volume of the first reservoir, i.e., at least about 35%. The insert has the overall appearance of a conic section, with a planar bottom, 41, and a circular side, 42, and is formed with a depression, 43, which extends downward from the top of the insert and functions as a second reservoir. The depression is dimensioned and shaped to closely rceivably accommodate the double well 13 and tower 11 extending into the lower portion 1 from the cover of the heated humidifier. The bottom of the depression or second reservoir may be in open communication with the first reservoir, although whether or not this is the case is unimportant for this embodiment. The insert has an upper and a lower portion, 44 and 46, respectively, which are connected by several solid posts or pillars, 47. Between the upper and lower portions is a gap, 46, which allows viewing of the water level since the second reservoir 43 extends through the upper portion into the lower portion. Typically, when the water level falls to a point near the bottom of said gap sterile water is manually added to the humidifier in a quantity sufficient to raise its level to or near the top of the gap.

What is claimed is:

1. In a heated humidifier used in respiratory therapy consisting of a first reservoir removably attached to a cover, said cover having: (a) an inlet port for gas entry, said port being the upper terminus of a first conduit leading into a tower open at its bottom and top, the tower containing a perforated disc near the bottom of said tower, the first conduit terminating at and being in open communication with the underside of the disc, said disc acting to disperse the gas entering the inlet port; (b) a gas exit port, and; (c) a double well the improvement consisting of a solid removable, space filling, volume reducing insert for said first reservoir constructed of a noncompressible, nonabsorbent, sterilizable material contoured to fit said first reservoir and dimensioned so as to occupy at least 35% of the volume of the first reservoir, the insert formed with a depression, in open communication at its bottom surface with the first reservoir, acting as a second reservoir receivably accommodating the double well and tower, a chamber formed on a side of the the insert adjacent to the second reservoir, a second conduit extending from its lower terminus at the upper portion of the chamber through the body of the insert to its upper terminus at the top of the insert, a float valve pivotally connected at one end to the top of said chamber, said valve having means to positively close the lower terminus of the second conduit.

2. The insert of claim 1 in which the upper terminus of the second conduit ends in a tapered bushing sealably receiving the lower terminus of a delivery tube of a water transfer set where the water transfer set consists of the delivery tube whose upper terminus is sealed to the open top portion of an elbow, a segment of flexible tubing connected in a watertight manner at its lower end to the top portion of said elbow and in open communication with the upper terminus of the delivery tube, said tubing connected at its upper end to a drip chamber having a cap terminating in a pointed, tubular puncture spike, said elbow having a lower end closely dimensioned to fit over the gas exit port, and said elbow having a lateral tubular portion terminating in an open port, said water transfer set providing a fluid path from the drip chamber to the lower terminus of the delivery tube.

3. In a heated humidifier used in respiratory therapy consisting of a first reservoir removably attached to a cover, said cover having: (a) an inlet port for gas entry, said port being the upper terminus of a first conduit leading into a tower open at its bottom and top, the tower containing a perforated disc near the bottom of said tower, the first conduit terminating at and being in open communication with the underside of the disc, said disc acting to disperse the gas entering the inlet port; (b) a gas exit port, and; (c) a double well the improvement consisting of a solid removable, space filling, volume-reducing insert for said first reservoir constructed of a noncompressible, nonabsorbent, sterilizable material contoured to fit said first reservoir and dimensioned so as to occupy at least 35% of the volume of the first reservoir, the insert formed with a depression acting as a second reservoir receivably accommodating the double well and tower, said insert having an upper and a lower portion separated by a gap with said upper and lower portion connected by a plurality of posts.

* * * * *